(12) United States Patent
Henderson

(10) Patent No.: US 6,719,784 B2
(45) Date of Patent: Apr. 13, 2004

(54) COUNTER ROTATIONAL LAYERING OF EPTFE TO IMPROVE MECHANICAL PROPERTIES OF A PROSTHESIS

(75) Inventor: Jamie S. Henderson, Oakland, NJ (US)

(73) Assignee: SciMed Life Systems, Inc., Maple Grove, MN (US)

(*) Notice: Subject to any disclaimer, the term of this patent is extended or adjusted under 35 U.S.C. 154(b) by 83 days.

(21) Appl. No.: 09/990,422

(22) Filed: Nov. 21, 2001

(65) Prior Publication Data

US 2003/0097174 A1 May 22, 2003

(51) Int. Cl.[7] .................................................. A61F 2/06
(52) U.S. Cl. ..................... 623/1.44; 623/1.13; 623/1.49
(58) Field of Search ............................. 623/1.39, 1.44, 623/1.49, 1.54, 23.64, 23.71, 1.13

(56) References Cited

U.S. PATENT DOCUMENTS

| | | |
|---|---|---|
| 2,945,265 A | 7/1960 | Sell, Jr. et al. |
| 3,008,187 A | 11/1961 | Slade |
| 3,260,774 A | 7/1966 | Harlow |
| 4,104,394 A | 8/1978 | Okita |
| 4,225,547 A | 9/1980 | Okita |
| 4,743,480 A | 5/1988 | Campbell et al. |
| 4,876,051 A | 10/1989 | Campbell et al. |
| 5,156,785 A | 10/1992 | Zdrahala |
| 5,505,887 A | 4/1996 | Zdrahala et al. |
| 5,788,626 A | * 8/1998 | Thompson .................. 623/1.15 |
| 5,800,512 A | 9/1998 | Lentz et al. |
| 5,824,046 A | 10/1998 | Smith et al. |
| 5,874,032 A | 2/1999 | Zdrahala et al. |
| 5,928,279 A | * 7/1999 | Shannon et al. ........... 623/1.13 |
| 6,027,779 A | 2/2000 | Lewis et al. |

FOREIGN PATENT DOCUMENTS

| | | |
|---|---|---|
| EP | 0 775 472 A | 5/1997 |
| WO | WO 97 02791 A | 1/1997 |
| WO | WO 00 43052 A | 7/2000 |

OTHER PUBLICATIONS

Copy of Search Report issued on Dec. 16, 2002 for International Application No. PCT/US 02/29291.

* cited by examiner

Primary Examiner—Paul B. Prebilic
(74) Attorney, Agent, or Firm—Hoffmann & Baron, LLP

(57) ABSTRACT

A prosthesis, and method for forming same, are provided which includes expanded polytetrafluoroethylene (ePTFE) tubes having angularly offset node and fibril configurations. Also, the node and fibril configurations are angularly offset from the longitudinal axes of the respective tubes, providing resistance against failure in the longitudinal direction.

7 Claims, 4 Drawing Sheets

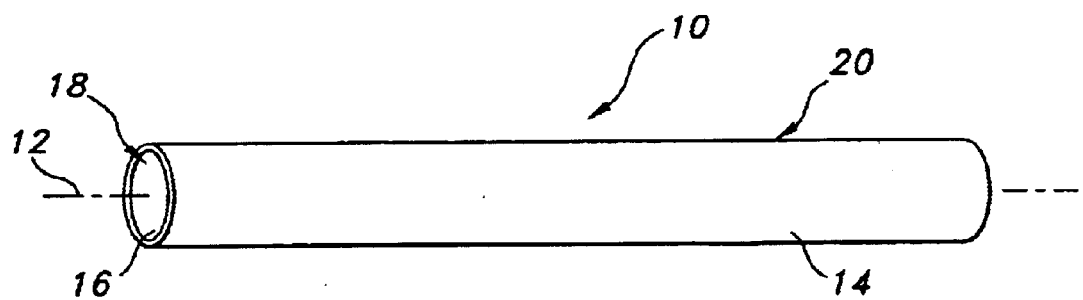
FIG. 1
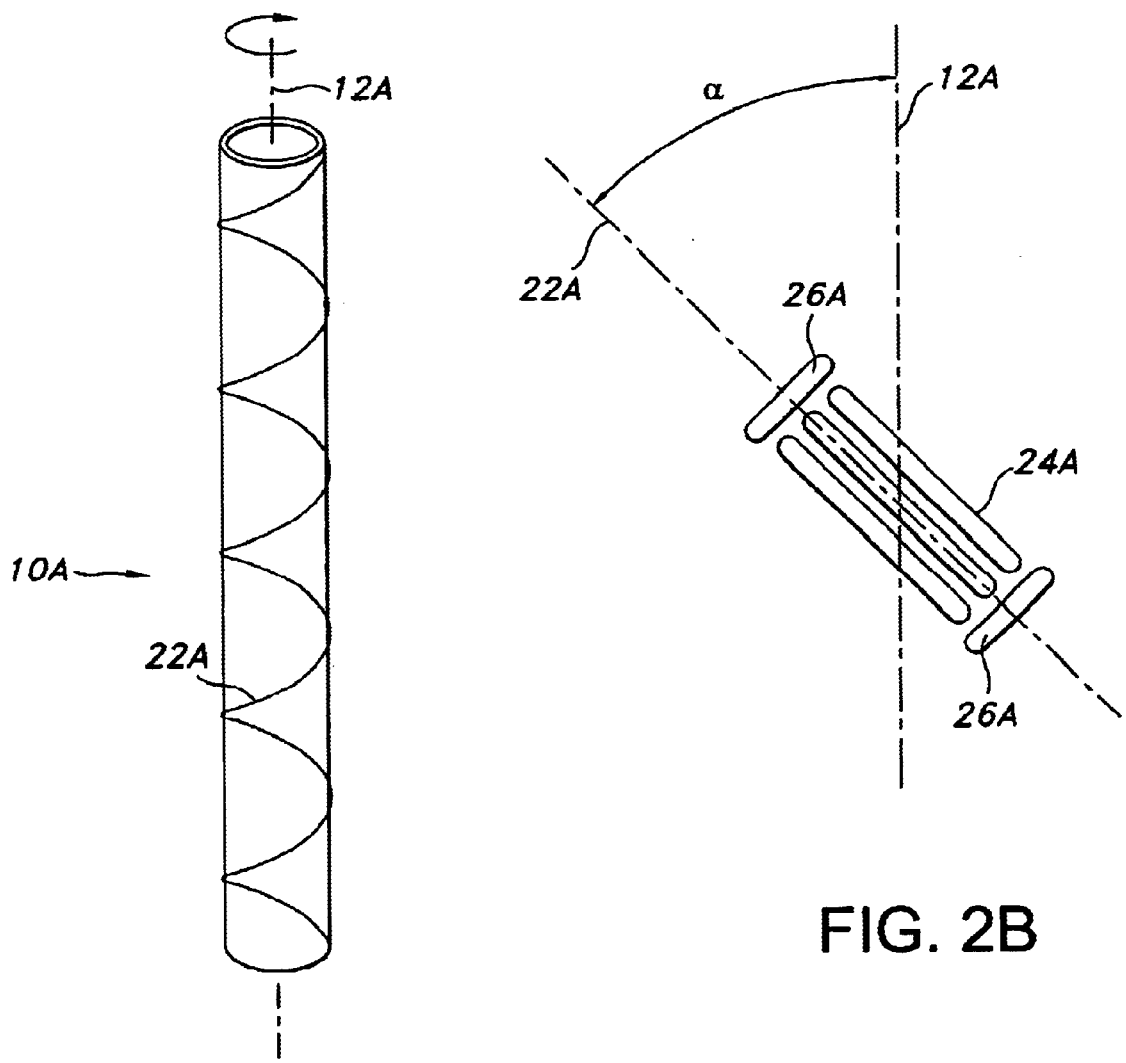
FIG. 2A
FIG. 2B

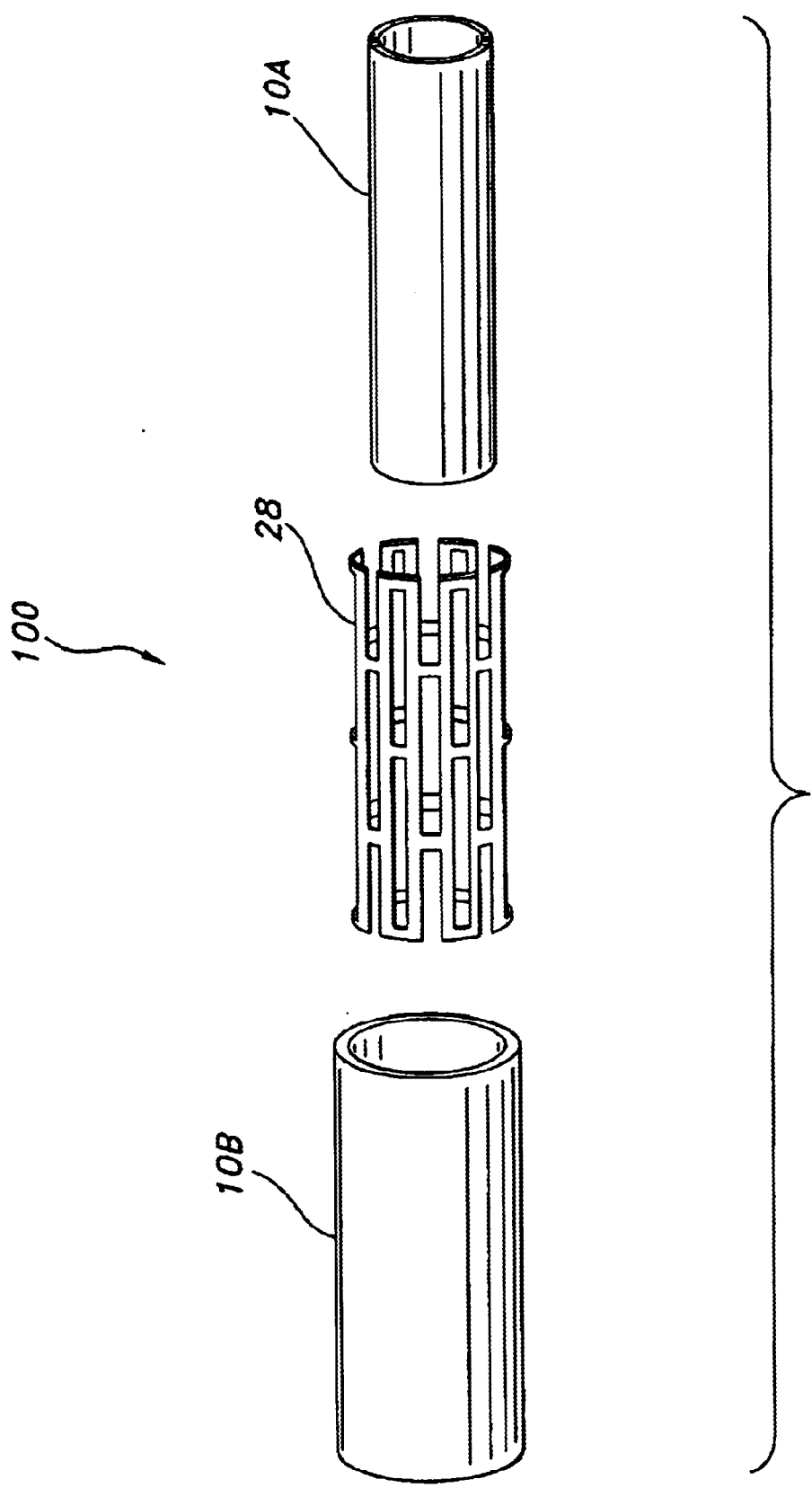

COUNTER ROTATIONAL LAYERING OF EPTFE TO IMPROVE MECHANICAL PROPERTIES OF A PROSTHESIS

FIELD OF THE INVENTION

This invention relates to methods of preparing tubular prostheses, and, more particularly, to techniques for forming multi-layered prostheses.

BACKGROUND OF THE INVENTION

Formation of prostheses from polytetrafluoroethylene (PTFE), particularly expanded polytetrafluoroethylene (ePTFE) is well known in the prior art. ePTFE includes a node and fibril structure, having longitudinally extending fibrils interconnected by transverse nodes. The nodes are not particularly strong in shear, and, thus, ePTFE structures are susceptible to failure in a direction parallel to the fibril orientation. ePTFE structures (tubes, sheets) are typically paste extruded, and, the fibrils are oriented in the extrusion direction.

Vascular grafts formed of ePTFE are well known in the art. Where sutures have been used to fix such grafts, suture hole elongation and propagation of tear lines from suture holes have been noted.

To overcome the deficiencies of the prior art, techniques have been developed which re-orient the node and fibril structure of an ePTFE element to be transverse to the extrusion direction. By orienting the fibrils at an angle relative to the extrusion direction, the tear strength of a respective product may be greatly improved. In one technique set forth in U.S. Pat. Nos. 5,505,887 and 5,874,032, both to Zdrahala et al., an extrusion machine is described having a counter-rotating die and mandrel arrangement. Accordingly, upon being extruded, a single-layer unitary PTFE tube is formed having an outer surface twisted in one helical direction, and an inner surface twisted in an opposite helical direction. Although tubes formed in accordance with the method of U.S. Pat. Nos. 5,505,887 and 5,874,032 are expandable to form an ePTFE structure, the fibrils of the structure are oriented generally parallel to the expansion direction after expanding as shown in the micrograph of FIG. 5 in U.S. Pat. No. 5,874,032. Also, the tube tends to thin out unevenly under expansion, and, suffers from "necking".

SUMMARY OF THE INVENTION

To overcome the deficiencies of the prior art, a method is provided wherein ePTFE tubes are counter-rotated, coaxially disposed, and fixed one to another to form a composite multi-layer prosthesis. By rotating the tubes, the tubes each becomes helically twisted with its node and fibril configuration being angularly offset throughout from the longitudinal axis of the tube (and, thus, angularly offset from the extrusion direction of the tube). With counter-rotation, the nodes and fibrils of the two tubes are also angularly offset from each other, resulting in a relatively strong composite structure. The composite multi-layer structure is akin to plywood, where alternating layers have differently oriented grain directions.

These and other features will be better understood through a study of the following detailed description and accompanying drawings.

BRIEF DESCRIPTION OF DRAWINGS

FIG. 1 is an elevational view of an ePTFE tube;

FIG. 2A is an elevational view of a helically wound tube twisted in a first rotational direction;

FIG. 2B is a schematic of the node and fibril orientation of the first tube in a helically wound state;

DETAILED DESCRIPTION OF THE INVENTION

Figure 3A:
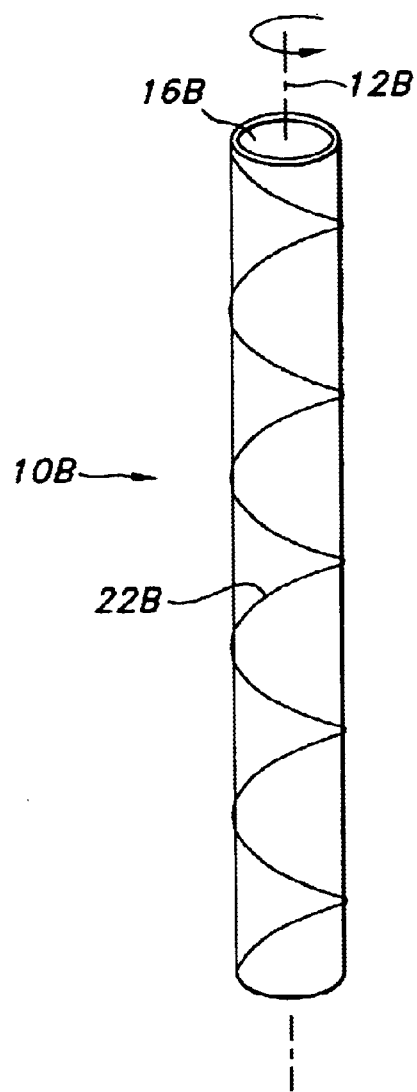
FIG. 3A is an elevational view of a helically wound tube twisted in a second rotational direction.

The invention herein provides a multi-layer prosthesis which may be used as a graft to replace a portion of a bodily passageway (e.g., vascular graft), or within a bodily passageway to maintain patency thereof, such as an endovascular stent-graft. In addition, the prosthesis can be used in other bodily applications, such as the esophagus, trachea, colon, biliary tract, urinary tract, prostate, and the brain.

The prosthesis is composed of multiple layers, including coaxially disposed ePTFE tubes. To illustrate the invention, reference will be made to the use of two ePTFE tubes, although any number may be utilized consistent with the principles disclosed herein. With reference to FIG. 1, an ePTFE tube 10 is shown which extends along a longitudinal axis 12. The ePTFE tube 10 is preferably formed by extrusion, thus having its fibrils generally parallel to the extrusion direction of the tube, which coincides with the longitudinal axis 12. The ePTFE tube 10 includes a wall 14 (which is seamless if extruded), that extends about a lumen 16. The wall 14 includes an inner luminal surface 18 facing the lumen 16, and an outer, abluminal surface 20. The ePTFE tube may be formed of any length and of various dimensions, although it is preferred that the dimensions be generally constant throughout the length thereof. In describing first and second tubes of the invention, like reference numerals will be used to describe like elements, but with the extensions "A" and "B" for differentiation. Elements associated with a first tube will have the extension "A", while elements associated with a second tube will have the extension "B".

Referring to FIG. 2A, a first ePTFE tube 10A is shown disposed along a longitudinal axis 12A. The first tube 10A is twisted about its longitudinal axis 12A in a first rotational direction, such as clockwise, as shown in FIG. 2A. The tube 10A may be twisted over any given range of degrees, although it is preferred that the tube be twisted at least 10 degrees. Accordingly, as represented by the hypothetical reference axis 22A, the first tube 10A is helically wound in the first rotational direction. As a result and as shown in FIG. 2B, fibrils 24A are generally parallel to the reference axis 22A, with the fibrils 24A being angularly offset an angle α from the longitudinal axis 12A, and, thus, being also angularly offset the angle α from the original extrusion direction of the first tube 10A. Nodes 26A are generally perpendicular to the fibrils 24A. With the fibrils 24A, and the nodes 26A, being obliquely disposed relative to the longitudinal axis 12A, failure along the longitudinal axis 12A may be reduced.

Figure 3B:
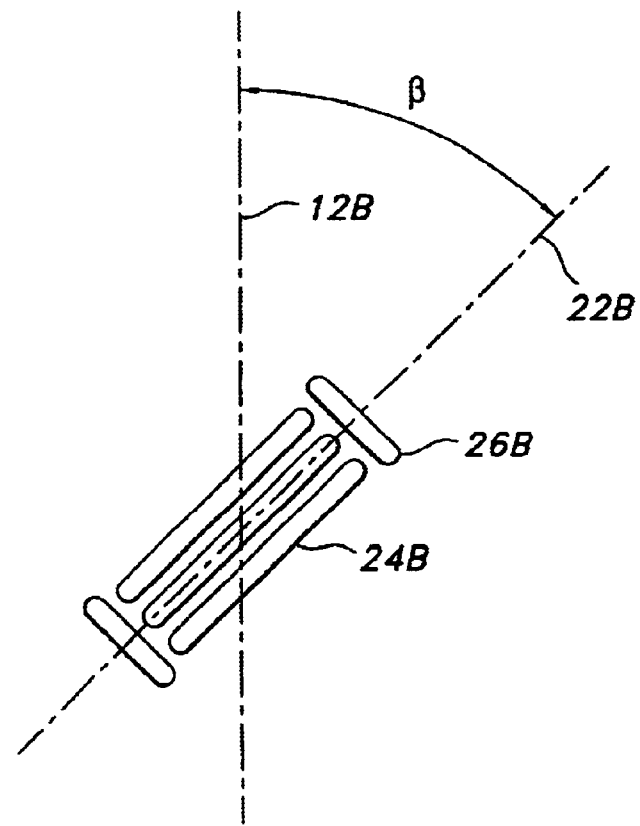
FIG. 3B is a schematic of the node and fibril orientation of the second tube in a helically wound state.

Referring to FIGS. 3A and 3B, a second ePTFE tube 10B is shown being twisted in a second rotational direction different than the first rotational direction of the first tube 10A. As shown in FIG. 3A, the second ePTFE tube is twisted in a counterclockwise direction. The particular rotational direction of twisting may be switched for the first and second tubes 10A and 10B. As with the first tube 10A, the amount of twisting of the second tube 10B may be varied, although it is preferred that at least a 10 degree displacement be provided. The helically wound distortion of the second tube 10B is represented by the hypothetical reference axis 22B. As shown in FIG. 3B, fibrils 24B are generally parallel to the reference axis 22B and are angularly offset an angle β from the longitudinal axis 12B (and, thus, the extrusion direction). Nodes 26B are generally perpendicular to the fibrils 26A. The oblique disposition of the fibrils 24B and the nodes 26B resists failure along the longitudinal axis 12B.

Figures 4A, 4B:
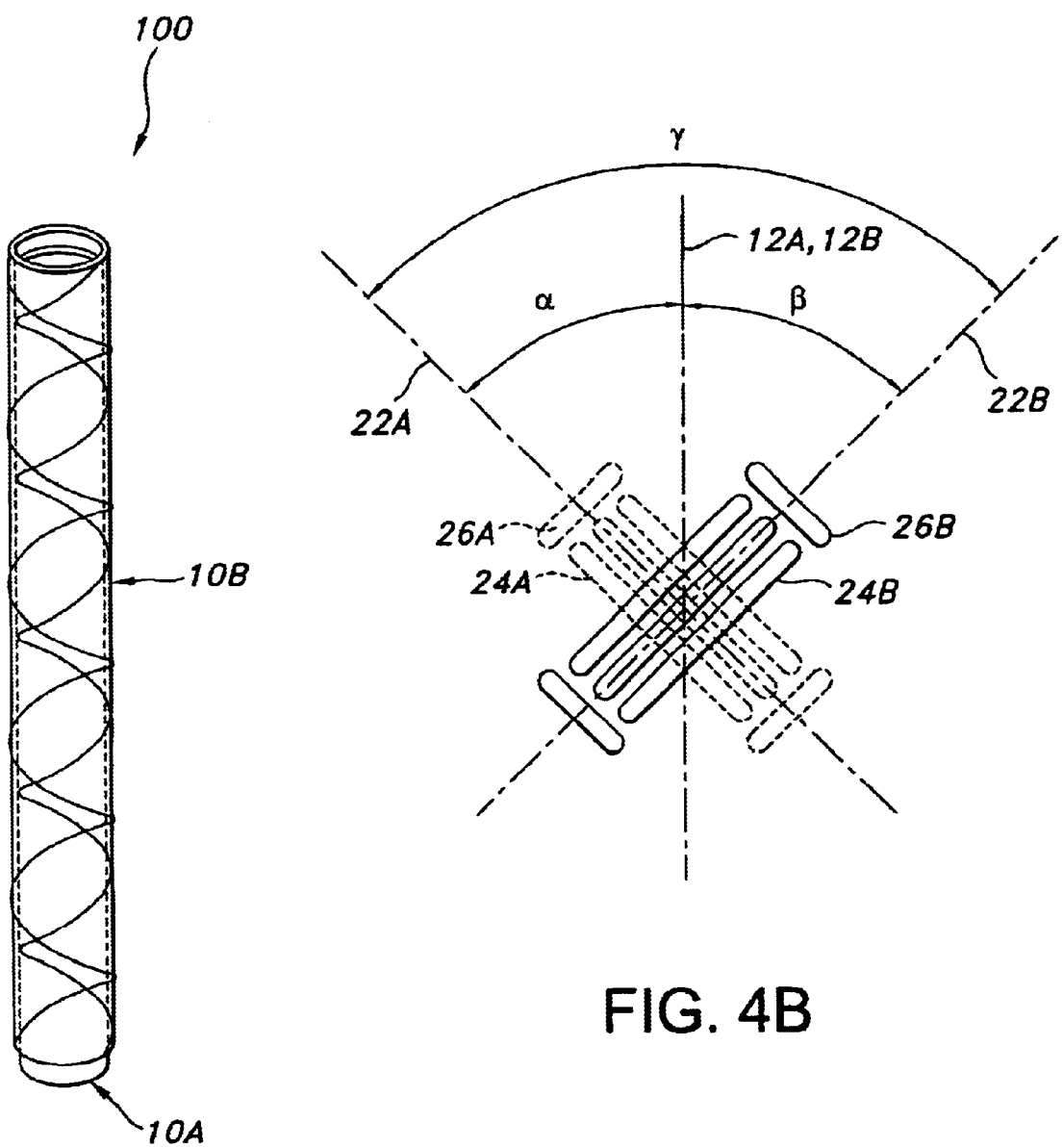
FIG. 4A is an elevational view of a prosthesis formed in accordance with the subject invention.
FIG. 4B is a schematic of the node and fibril orientations of the composite prosthesis; and, FIG. 5 is an exploded view of a prosthesis having a radially-expandable support member.

FIG. 4A shows a prosthesis 100 including the first tube 10A, in its twisted helical state being coaxially disposed within, and fixed to, the second tube 10B, in its twisted helical state. It is preferred that the tubes 10A and 10B be generally coextensive, although the ends of the tubes need not be coterminous. Because of the different rotational orientations of the node and fibril structures of the tubes 10A and 10B, the node and fibril structures are angularly offset from each other. In particular, as shown schematically in FIG. 4B, because of the coaxial arrangement of the tubes 10A, 10B, the longitudinal axes 12A and 12B are generally colinear. Also, the fibrils 24A of the first tube 10A are angularly offset from the fibrils 24B of the second tube 10B by an angle γ. The angular offset of the fibrils 24A and 24B provides the prosthesis 100 with resistance against failure not provided by either tube 10A, 10B alone. In a preferred embodiment, with the angles α and β being each at least 10 degrees, the angle γ will be at least 20 degrees. Preferably, the node and fibrils of each of the tubes 10A, 10B are generally-equally angularly offset throughout the respective tube 10A, 10B.

Because the first tube 10A is disposed within the second tube 10B, the second tube 10B is formed dimensionally slightly larger to accommodate the first tube 10A within its lumen 16B.

As an alternative, only one of the tubes 10A, 10B may be twisted. The node and fibrils of the two tubes 10A, 10B would, nevertheless, be angularly offset.

In a preferred manner of preparing the prosthesis 100, the first tube 10A is provided and mounted onto a mandrel where it is twisted into its desired helical configuration. The twisted configuration of the first tube 10A is maintained. The second tube 10B is provided and twisted as desired, and in its twisted state telescoped over the first tube 10A. The first and second tubes 10A and 10B are fixed together using any technique known to those skilled in the art, preferably sintering. Adhesive may also be used to bond the tubes, such as a thermoplastic fluoropolymer adhesive (e.g., FEP). Once fixed, the prosthesis 100 is prepared.

Although reference has been made herein to extruded ePTFE tubes, tubes formed by other techniques may also be used, such as with rolling a sheet, or wrapping a tape. Generally, with these non-extrusion techniques, the fibrils of the ePTFE will not initially be oriented parallel to the longitudinal axis of the tube, but rather transverse thereto. These non-extruded tubes may replace one or more of the tubes 10A, 10B in a non-twisted state or in a twisted state.

As shown in FIG. 5, the prosthesis 100 may also include a radially expandable support member 28, which may be disposed interiorly of the first tube 10A, exteriorly of the second tube 10B, or interposed between the two tubes 10A, 10B. Additionally, multiple support members located at the aforementioned locations may be provided. The radially expandable support member 28 may be fixed to the tubes 10A, 10B using any technique known to those skilled in the art, such as bonding. Additionally, with the radially expandable support member 28 being interposed between the tubes 10A, 10B, the tubes 10A, 10B may be fixed together through any interstices formed in the radially expandable support member 28.

The radially expandable support member 28 may be of any construction known in the prior art which can maintain patency of the prosthesis 100. For example, as shown in FIG. 5, the radially-expandable support member 28 may be a stent. The particular stent 28 shown in FIG. 5 is fully described in commonly assigned U.S. Pat. No. 5,693,085 to Buirge et al., and the disclosure of U.S. Pat. No. 5,693,085 is incorporated by reference herein. The stent may be an intraluminally implantable stent formed of a metal such as stainless steel or tantalum, a temperature-sensitive material such as Nitinol, or alternatively formed of a superelastic alloy or suitable polymer. Although a particular stent construction is shown with reference to the present invention, various stent types and stent constructions may be employed for the use anticipated herein. Among the various useful radially-expandable support members 28 include, without limitation, self-expanding stints and balloon expandable stints. The stints may be capable of radially contracting as well. Self-expanding stints include those that have a spring-like action which causes the stent to radially expand or stints which expand due to the memory properties of the stent material for a particular configuration at a certain temperature. Other materials are of course contemplated, such as stainless steel, platinum, gold, titanium, tantalum, niobium, and other biocompatible materials, as well as polymeric stints. The configuration of the radially-expandable support member 28 may also be chosen from a host of geometries. For example, wire stints can be fastened in a continuous helical pattern, with or without wave-like forms or zig-zags in the wire, to form a radially deformable stent. Individual rings or circular members can be linked together such as by struts, sutures, or interlacing or locking of the rings to form a tubular stent.

Furthermore, the prosthesis 100 may be used with additional layers which may be formed of polymeric material and/or fabric. Furthermore, any layer or portion of the prosthesis 100, including the tubes 10A, 10B, may be impregnated with one or more therapeutic and pharmacological substances prior to implantation of the prosthesis 100 for controlled release over an extended duration. It is anticipated that the prosthesis 100 can be partially or wholly coated with hydrophilic or drug delivery-type coatings which facilitate long-term healing of diseased vessels. Such a coating is preferably bioabsorbable, and is preferably a therapeutic agent or drug, including, but not limited to, anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, antithrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasco-active mechanisms.

Various changes and modifications can be made in the present invention. It is intended that all such changes and modifications come within the scope of the invention as set forth in the following claims.

What is claimed is:

1. A prosthesis comprising:
   a first ePTFE tube in a helically twisted state oriented in a first rotational direction, wherein said first tube having been twisted from an initial state, with a first point on a first end of said first tube being longitudinally aligned along a first longitudinal reference axis with a second point on a second end of said first tube, to said helically twisted state, with at least one of said first and second points having been angularly displaced from said first longitudinal reference axis; and,
   a second ePTFE tube disposed coaxially within said first tube, said second tube being in a helically twisted state oriented in a second rotational direction different from said first rotational direction, wherein said second tube having been twisted from an initial state, with a first point on a first end of said second tube being longitudinally aligned along a second longitudinal reference axis with a second point on a second end of said second tube, to said helically twisted state, with at least one of said first and second points having been angularly displaced from said second longitudinal reference axis.

2. A prosthesis as in claim 1, wherein said first tube is fixed to said second tube.

3. A prosthesis comprising:
   a first ePTFE tube having a node and fibril structure; and,
   a second ePTFE tube disposed coaxially within said first tube, said second tube being in a helically twisted state and having a node and fibril structure, wherein said second tube having been twisted from an initial state, with a first point on a first end of said second tube being longitudinally aligned along a longitudinal reference axis with a second point on a second end of said second tube, to said helically twisted state, with at least one of said first and second points having been angularly displaced from said longitudinal reference axis, and wherein said node and fibril structure of said second tube being angularly offset from said node and fibril structure of said first tube.

4. A prosthesis as in claim 3, wherein said first tube is in a helically twisted state oriented in a first rotational direction different from said second tube.

5. A prosthesis as in claim 3, wherein said first tube extends along a first longitudinal axis, and said node and fibril structure of said first tube is angularly offset from said first longitudinal axis.

6. A prosthesis as in claim 3, wherein said second tube extends along a second longitudinal axis, and said node and fibril structure of said second tube is angularly offset from said second longitudinal axis.

7. A prosthesis as in claim 3, wherein said first tube is fixed to said second tube.

* * * * *